US006833361B2

(12) United States Patent
Hong et al.

(10) Patent No.: US 6,833,361 B2
(45) Date of Patent: *Dec. 21, 2004

(54) NUCLEOSIDES HAVING BICYCLIC SUGAR MOIETY

(75) Inventors: Zhi Hong, Aliso Viejo, CA (US); Haoyun An, Carlsbad, CA (US)

(73) Assignee: Ribapharm, Inc., Costa Mesa, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/136,932

(22) Filed: Apr. 30, 2002

(65) Prior Publication Data

US 2003/0028013 A1 Feb. 6, 2003

Related U.S. Application Data

(63) Continuation-in-part of application No. 09/451,708, filed on Dec. 1, 1999, now Pat. No. 6,403,566, which is a continuation of application No. PCT/US99/11442, filed on May 24, 1999.
(60) Provisional application No. 60/086,719, filed on May 26, 1998.

(51) Int. Cl.$^7$ .......................... A61K 31/70; A01N 43/04
(52) U.S. Cl. .......................... 514/45; 514/46; 514/47; 514/48; 514/49; 514/50; 514/51; 536/26.7; 536/26.8
(58) Field of Search .......................... 514/45, 46, 47, 514/48, 49, 50, 51; 536/26.7, 26.8

(56) References Cited

U.S. PATENT DOCUMENTS 6,403,566 B1 * 6/2002 Wang .......................... 514/45

FOREIGN PATENT DOCUMENTS

WO     WO 99/14226     3/1999

OTHER PUBLICATIONS

Altmann, K., et al. 4',6'–Methano Carbocyclic Thymidine: A Conformationally Constrained Building Block for Oligonucleotides. Tetrahedron Letters (1994), 35(15):2331–2334.
Hong, J.H., et al. Synthesis of Novel D–2',3'–Dideoxy–2',3' endo–methylene Nucleosides. Tetrahedron Letters (1998), 39: 225–228.
Obika, S., et al. Synthesis of 2'–O,4'–C–Methyleneuridine and –cytidine. Novel bicyclic Nucleosides Having a Fixed C3 –endo Sugar Puckering. Tetrahedron Letters (1997), 38(50).

* cited by examiner

Primary Examiner—Samuel Barts
Assistant Examiner—Patrick Lewis
(74) Attorney, Agent, or Firm—Brown, Raysman, Millstein Felder & Steiner LLP

(57) ABSTRACT

Conformationally restricted 2', 4'-bridged nucleoside analogues are described herein. The compounds can be prepared by cyclization at C2' and C4' of nucleosides through a linker or linking molecule. These novel nucleosides have a desired, locked sugar pucker and are potentially useful as pharmaceutical ingredients, and especially for use in treatment of HCV.

11 Claims, No Drawings

NUCLEOSIDES HAVING BICYCLIC SUGAR MOIETY

PRIORITY

This application is a Continuation in Part (CIP) of application Ser. No. 09/451,708, filed Dec. 1, 1999, issued as U.S. Pat. No. 6,403,566, on Jun. 11, 2002, which was a continuation of PCT/US99/11442, filed May 24, 1999, designating the United States and which claimed priority to provisional application No. 60/086,719, filed May 26, 1998.

FIELD OF THE INVENTION

The field of the invention is nucleoside analogues and methods of their use.

BACKGROUND

Nucleoside and nucleotide analogs have long been used as pharmaceutical ingredients against a variety of viruses and cancers. Currently, a number of nucleoside and nucleotide analogues are in clinical trials for several diseases.

In the cell, nucleosides and nucleotides are phosphorylated or further phosphorylated to the corresponding nucleoside triphosphates. Nucleoside triphosphates serve as inhibitors of DNA or RNA polymerases. Nucleoside triphosphates can also be incorporated into DNA or RNA, which interferes with the elongation of DNA or RNA.

Active nucleoside analogues are generally readily phosphorylated in the target cell. Corresponding nucleoside triphosphates have a high affinity to catalytic sites of the polymerases and compete with the natural nucleoside triphosphates as the substrate of the polymerases.

Certain nucleoside analogues work at the nucleoside or the monophosphate level. One group of promising nucleoside analogues is the nucleosides with conformationally locked sugar moieties. It has been reported that certain conformationally locked carbocyclic nucleoside analogues demonstrated potent activity against HCMV, HSV, and EBV (Siddiqui et al. *Nucleosides Nucleotides* 1996, 15, 235–250; Marquez et al. *J. Med. Chem.* 1996, 39, 3739–3747). A conformationally locked, carbocyclic AZT 5'-triphosphate has been reported to be an equipotent inhibitor of HIV reverse transcriptase (Marquez et al. *J. Am. Chem. Soc.* 1998, 120, 2780–2789). Other nucleosides with bicyclic sugar moieties were also prepared even though no activity was found or reported (Chao et al. *Tetrahedron* 1997, 53, 1957–1970; Okabe et al. *Tetrahedron lett.* 1989, 30, 2203–2206, Hong, et al. *Tetrahedron Lett.* 1998, 39, 225–228).

Favorable, conformationally locked nucleosides are expected to have a positive impact on antisense oligonucleotides. Oligonucleotides, as potential antisense therapeutics, have been recognized and explored for two decades. Oligonucleotides are capable of forming a double or triple helix with complementary DNA or RNA and have the ability to target the specific sequences in the viral and cancer genome. Specific binding of oligonucleotides to the DNA or RNA targets of interest would inactivate the function associated with the DNA or RNA such as replication, transcription, and translation. Therefore, viral cycles, or cancerous processes can be interrupted while the normal cell cycles are not affected.

Since natural oligonucleotides are labile to the cellular and extracellular nucleases, a great deal of efforts has been made on the study of oligonucleotide modifications, especially those modifications aimed at improving nuclease resistance and binding affinity. Oligonucleotides containing certain bicyclic nucleosides have been shown to demonstrate improved nuclease stability (Leumann et al. *Bioorg. Med. Chem. Letts.* 1995, 5, 1231–4; Altmann et al. *Tetrahedron Lett.* 1994, 35, 2331–2334, 7625–7628). Recently, 2'-O, 4'-C-methylene ribonucleosides, which have a locked 3'-endo sugar pucker, were synthesized and incorporated into oligonucleotides. Hybridization studies show that conformationally locked nucleosides can significantly enhance hybridization of modified oligonucleotides to the complementary RNA and DNA (Obika et al. *Tetrahedron Lett.* 1997, 38, 8735–8738; Koshkin et al. *Tetrahedron* 1998, 54, 3607–3630).

There is a need for new, conformationally locked nucleosides with bicyclic sugar moieties. These novel nucleosides should be useful in antiviral, anti-cancer, and other therapies.

SUMMARY OF THE INVENTION

Conformationally locked bicyclic-sugar nucleosides, which have a common geometrical shape, and methods for producing conformationally locked bicyclic-sugar nucleosides are described. Nucleosides are provided having bicyclic sugar moieties and oligonucleotides comprising the following formula:

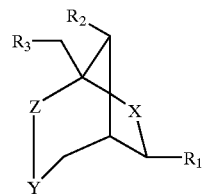

Wherein X, Y and Z are independently selected from a group of O, S, $CH_2$, NR, C=O, C=$CH_2$ or nothing, where R is selected from a group of hydrogen, alkyl, alkenyl, alkynyl, acyl; $R_1$ is selected from a group of adenine, cytosine, guanine, hypoxanthine, uracil, thymine, heterocycles, H, $OCH_3$, OAc, halogen, sulfonate; $R_2$, $R_3$ are independently selected from a group of H, OH, DMTO, TBDMSO, BnO, THPO, AcO, BzO, OP(NiPr$_2$)O(CH$_2$)$_2$CN, OPO$_3$H, PO$_3$H, diphosphate, triphosphate; $R_2$ and $R_3$ together can be PhCHO$_2$, TIPDSO$_2$ or DTBSO$_2$.

The novel nucleosides described herein are anticipated to be useful in antiviral, anti-cancer, and other therapies. Oligonucleotides composed of these modified nucleosides have desired physiological stability and binding affinity that enable them to be useful in therapeutics and diagnostics.

DETAILED DESCRIPTION

Conformationally locked nucleosides, which have a 3'-endo sugar pucker, and methods of their preparation and use are provided. Processes for preparation of previously reported bicyclic nucleoside analogues cannot be applied to the novel nucleoside analogues described herein. The analogues described resulted from the successful linking between the C2' and C4' positions of ribose in the nucleoside analogues.

As used herein, the abbreviation "Ac" refers to acetyl; the abbreviation "Bn" refers to benzyl; the abbreviation "Bz" refers to benzoyl; the abbreviation "DMT" refers to dimethoxytrityl; the abbreviation "THP" refers to tetrahydropyranyl; the abbreviation "TBDMS" refers to t-butyldimethylsilyl; the abbreviation "TIPDS" refers to tetraisopropyldisilyl; and the abbreviation "DTBS" refers to di(t-butyl)silyl.

Contemplated Compounds

Compounds generally contemplated herein include conformationally locked nucleosides which have a 3'-endo sugar pucker, and more specifically compounds with the general formula according to structure 1 below:

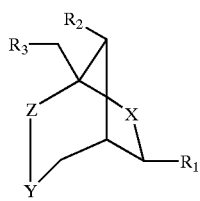

In particularly preferred aspects, contemplated compounds include a ribofuranose as the sugar moiety of the nucleoside. Consequently, a particularly suitable substituent X is oxygen. However, it should be recognized that various alternative sugar moieties are also appropriate, and it is generally contemplated that modified sugars and carbocyclic moieties are also considered suitable for use herein. Therefore, X may also include an atom or group other than oxygen, and especially contemplated alternative groups X include S where the sugar is a sulfur sugar, $CH_2$, C=O, C=$CH_2$ or a covalent bond where the sugar is a carbocyclic compound, and NR (with R selected from the group consisting of hydrogen, alkyl, alkenyl, alkynyl, aryl, and acyl) where the sugar is an amino sugar.

Similarly, the groups Y and Z may vary considerably, and the particular choice of the substituent Y and Z will at least partially depend on the particular choice of steric properties and/or hydrogen bond donor/acceptor properties in the desired compounds. However, particularly preferred substituents Y and Z include O, S, $CH_2$, NR, C=O, C=$CH_2$ or a covalent bond, wherein R is selected from the group consisting of hydrogen, alkyl, alkenyl, alkynyl, aryl, and acyl.

With respect to the substituent $R_1$, it is generally contemplated that all heterocyclic bases are suitable for use herein. The term "heterocyclic base" as used herein refers to a compound in which a plurality of atoms (wherein at least one atom is an atom other than a carbon atom) form a ring via a plurality of covalent bonds. However, particularly contemplated heterocyclic bases have between one and three rings, wherein especially preferred rings include 5- and 6-membered rings with nitrogen, sulfur, or oxygen as the non-carbon atom (e.g., imidazole, pyrrole, triazole, dihydropyrimidine). Further contemplated heterocyclic bases may be bound (e.g., covalently bound) to another ring or heterocycle, and are thus termed "fused heterocycle(s)" as used herein. Especially contemplated fused heterocycles include a 5-membered ring fused to a 6-membered ring (e.g., purine, pyrrolo[2,3-d]pyrimidine), a 6-membered ring fused to another 6-membered or higher ring (e.g., pyrido[4,5-d] pyrimidine, benzodiazepine), substituted and unsubstituted deazapurines, azapurines, deazapyrimidines, azapyrimidines.

Consequently, especially contemplated heterocyclic bases include a substituted or unsubstituted purine, a substituted or unsubstituted pyrimidine, a substituted or unsubstituted deazapurine, and a substituted or unsubstituted triazole. The term "substituted" as used herein refers to addition of one or more functional groups, wherein particularly contemplated functional groups include nucleophilic (e.g., —$NH_2$, —OH, —SH, —NC, etc.) and electrophilic groups (e.g., C(O)OR, C(X)OH, etc.), polar groups (e.g., —OH), non-polar groups (e.g., aryl, alkyl, alkenyl, alkynyl, etc.), ionic groups (e.g., —$NH_3^+$), and halogens (e.g., —F, —Cl), and all chemically reasonable combinations thereof.

In still further contemplated aspects, $R_2$ and $R_3$ may vary considerably, and a particular choice of $R_2$ and/or $R_3$ will depend at least in part on the choice of a particular sugar (supra). However, it is generally preferred at least one of $R_2$ and $R_3$ is H or OH (optionally protected). In still other contemplated aspects, suitable $R_2$ and/or $R_3$ may be independently selected from —Oalkyl, especially from —$OCH_3$, alkyl, and especially methyl, —Oacyl, —$N_3$, —CN, and halogen. Furthermore, where contemplated nucleoside analogs include a phosphate or phosphonate group, it is contemplated that especially suitable $R_2$ and/or $R_3$ groups include a monophosphate, diphosphate, triphosphate, monophosphonate, diphosphonate, triphosphonate, an amino acid ester with a sugar OH group, or a prodrug of the monophosphate, diphosphate, triphosphate, monophosphonate, diphosphonate, or triphosphonate.

Synthesis of Contemplated Compounds

The compounds generally contemplated herein include conformationally locked nucleosides, and it should be recognized that there are numerous alternative methods of synthesizing such compounds besides the following exemplary synthetic strategies. For example, where alternative heterocyclic bases are desired in the conformationally locked nucleosides, it should be recognized that all or almost all of the heterocyclic bases may be coupled to the sugar moiety following various protocols well known in the art. For example, suitable protocols and methods can be found in "Nucleoside Synthesis: Organosilicon Methods" by Edmund Lukevics (Ellis Horwood Ltd; ISBN: 0138126526), or in "Handbook of Nucleoside Synthesis" by Helmut Vorbruggen, and Carmen Ruh-Pohlenz (Wiley-Interscience; ISBN: 0471093831).

Particularly contemplated alternative heterocyclic bases include substituted or unsubstituted purine, a substituted or unsubstituted pyrimidine, a substituted or unsubstituted deazapurine, and a substituted or unsubstituted triazole. Thus, exemplary heterocyclic bases include all natural nucleobases in DNA and various RNA species (e.g., tRNA, snRNA, rRNA), heterocyclic bases of nucleoside analogs (e.g., 8-substituted purines, deazapurines, etc.), and heterocyclic bases as outlined above. Therefore, and at least in part dependent on the particular heterocyclic base, coupling of the heterocyclic base may involve a C—C bond or a C-heteroatom bond (e.g., C—N, or C—S). Furthermore, it should be recognized that all or almost all of the heterocyclic bases are commercially available.

Similarly, contemplated nucleosides need not be restricted to including a ribofuranose as the sugar portion, and numerous alternative sugars and sugar analogs are also contemplated. Most of such alternative sugars and sugar analogs are commercially available. However, where contemplated sugars are not commercially available, it should be recognized that there are various methods known in the art to synthesize such sugars. For example, suitable protocols can be found in "Modern Methods in Carbohydrate Synthesis" by Shaheer H. Khan (Gordon & Breach Science Pub; ISBN: 3718659212), in U.S. Pat. Nos. 4,880,782 and 3,817,982, in WO88/00050, or in EP199,451. Furthermore, all of the contemplated sugars may be in D- or L-configuration, wherein at least one of the substituents may further be in either alpha or beta orientation.

In particularly preferred compounds, the sugar portion includes a phosphate and/or phosphonate group as a C3' and/or C5' substituent. With respect to coupling of such groups, it should be appreciated that numerous synthetic protocols may be appropriate, and among alternative protocols, it is generally preferred that the phosphate and/or phosphonate group is coupled to the sugar via esterification with an OH group using protocols well known in the art. Furthermore, contemplated compounds, and especially those including a phosphate and/or phosphonate group may be modified to form a prodrug (which may or may not be liver-specific), and especially preferred prodrugs include amino acid esters and/or cyclic phosphate and/or phosphonates. Exemplary synthesis of such prodrugs is described, for example, in U.S. Pat. No. 6,277,830 to Ganguly et al., WIPO publication No. WO 00/52015, and WIPO publication No. WO 01/18013, all of which are incorporated by reference herein.

Synthesis of 2,4-Bridged Ribofuranose Derivatives
(Schemes 1 and 2)

1-α-Methylarabinose 1, prepared according to a published procedure (Tejima et al. *J. Org. Chem.* 1963, 28. 2999–3003), was protected with 1,1,3,3-tetraisopropyldisiloxanyl (TIPS) at O3 and O5 to give 2, which was converted to the ketone 3 by treatment with DMSO/DCC/TFA. The subsequent Wittig reaction and removal of TIPS afforded the alkene 4 in very good yield. Compound 4 was protected with t-butyldimethylsilyl (TBS) at O5 and with benzyl (Bn) at O3 to give 5. Hydroboration of 5 was conducted with 9-BBN to give exclusively the 2-deoxy-2-hydroxymethyl derivative 6 in excellent yield. 2-deoxy-2-hydroxymethyl derivative 6 was subjected to tritylation with 4,4'-O-dimethoxytrityl (DMT) chloride and removal of TBS with tetrabutylammonium fluoride (TBAF) to yield 7.

Scheme 1

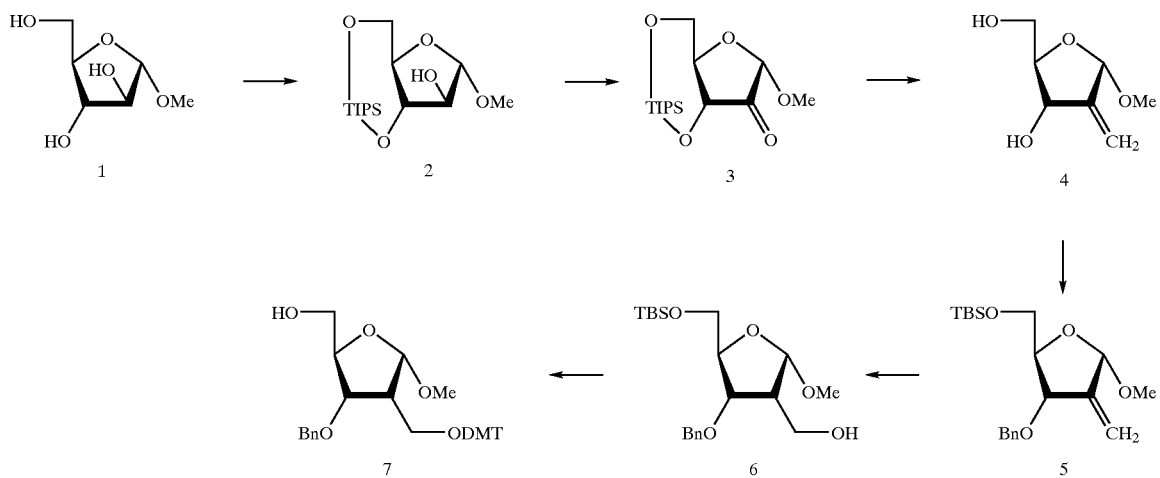

Alternatively, where it is desirable that the group Y is an atom other than oxygen, it is contemplated that compound 5 is reacted (e.g., using the C2'-methylidene group as an electrophilic reagent) with a reagent to yield a C2'-CH$_2$SH or C2'-CH$_2$NR group (wherein R is hydrogen, or substituted or unsubstituted alkyl, alkenyl, alkynyl, or aryl, or acyl). There are numerous methods for such reactions known in the art, and all of them are contemplated suitable for use herein.

To form the C2'–4' bridge, compound 7 was oxidized to give the aldehyde 8, which was treated with formaldehyde and sodium hydroxide to yield the 4-hydroxymethyl derivative 9 in excellent yield. The mesylation of 9 and the subsequent removal of DMT afforded 10. The cyclization effected with NaH in THF and the subsequent removal of the mesyl afforded the bicyclic sugar 11. Treatment of compound 11 with acetic anhydride in the presence of DMAP yields 12, whereas treatment with acetic anhydride/acetic acid in the presence of sulfuric acid yields 13, in which the acetoxy at C1 has an inverted orientation (1-β), as compared to the methoxy of 11.

Scheme 2

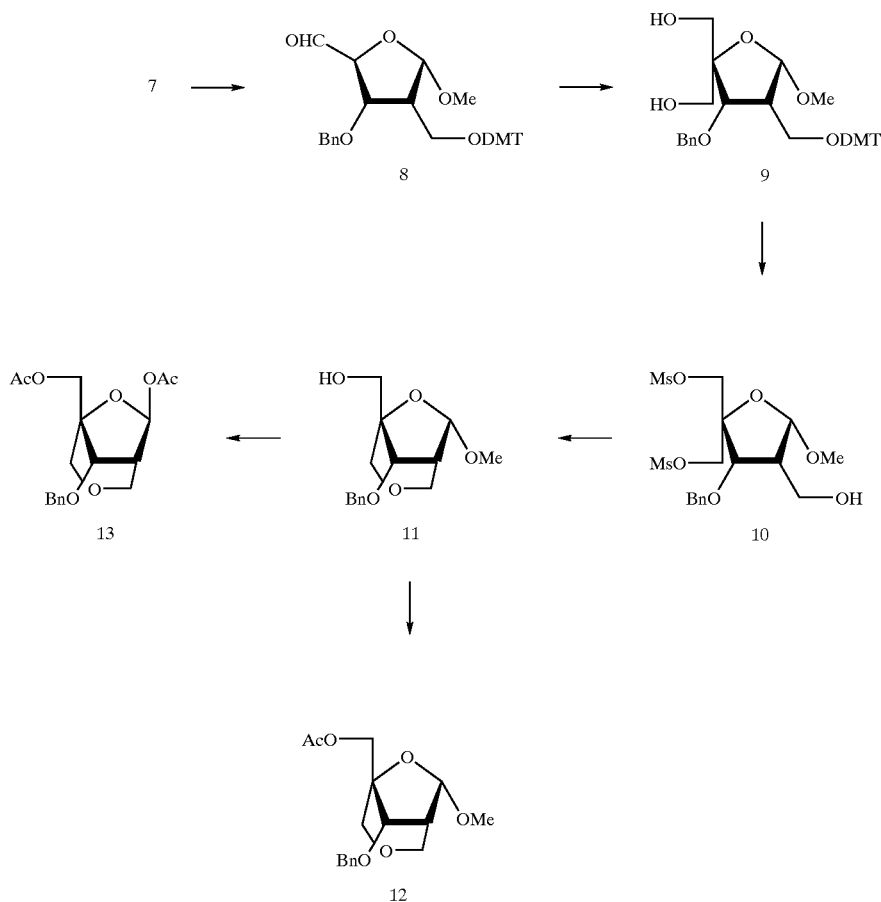

Furthermore, where it is desirable that the group Z is an atom other than a methylene group, it is contemplated that compound 5 is reacted (e.g., using the C2'-methylidene group as an electrophilic reagent) with a reagent to yield a C2'-CH$_2$YZ group (wherein Y is as defined above and Z is a nucleophilic group, including OH, SH, NH$_2$, and NHR, with R being hydrogen, or aryl, or acyl). There are numerous methods contemplated suitable for use herein.

Synthesis of 2',4'-Bridged Bicyclonucleosides

It should generally be recognized that the bicyclonucleosides having the 2',4'-bridged sugar moiety can be synthesized from condensations of a silylated nucleoside base and the bicyclic sugars as shown below. While the synthetic schemes below indicate use of particular bases, it should be appreciated that numerous alternative heterocyclic bases (see above) are also suitable for the condensation reactions depicted herein. Furthermore, while the below shown reactions employ a particular condensation reaction, various alternative routes are also considered appropriate.

The condensation of 13 with bis(trimethylsilyl)thymine yielded the product 14, the α-anomer, in excellent yield. Treatment of 14 with BCl$_3$ removed acetyl and benzyl simultaneously to yield the bicyclic α-thymidine 15.

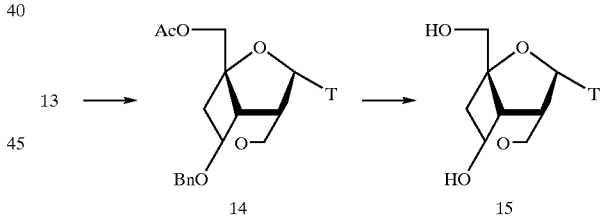

The condensation of 13 with 6-chloro-9-trimethylsilylpurine gave a mixture of the α- and β-purine nucleosides, 16 and 17 (ratio of α: β, 1:1 to 2:3), which could be separated by chromatography.

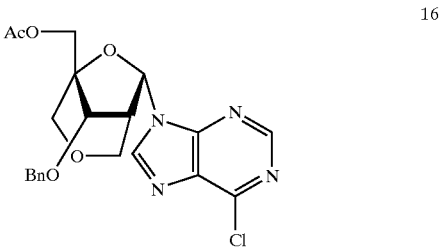

-continued

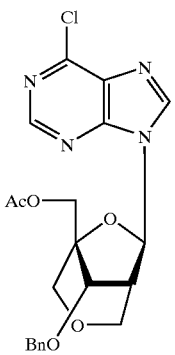

17

Treatment of 17 and 16 with ammonia in methanol, followed by hydrogenolysis, gave the adenosine analogs 18 and 19, respectively. The hydrogenolysis required a large amount of catalyst material, as well as a prolonged reaction time, because of the increased steric hindrance on the sugar moiety. Treatment of 17 and 16 with mercaptoethanol in the presence of sodium methoxide, followed by hydrogenolysis, yields inosine analogs 20 and 21, respectively.

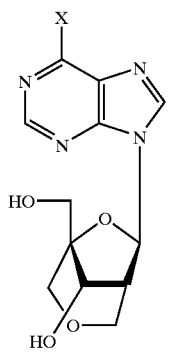

18 X = NH$_2$
20 X = OH

19 X = NH$_2$
21 X = OH

Condensation of 13 with the silylated N$^2$-acetylguanine yields the α-guanosine derivative 22 as the major product (30%), a small amount of the β-isomer and N$^7$-coupled products. Treatment of the α-guanosine derivative with ammonia in methanol, followed by hydrogenolysis, gave the bicyclic α-guanosine 23.

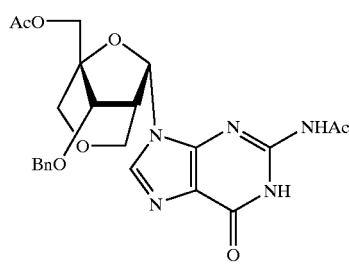

22

-continued

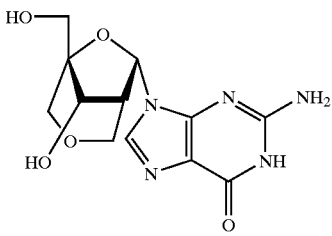

23

As described above, the condensation reactions yielded either the α-nucleoside, exclusively, or a mixture of the α- and β-nucleosides, without preference for the β-anomers. In order to increase the ratio of β-nucleosides, different condensation conditions were investigated. Temperature had little effect on the ratio of α- and β-anomers. However, the coupling reagent and the functional group at C1 of the sugar did have significant effects on the ratio of α- and β-nucleosides.

Condensation of 12 with bis- or tri(trimethylsilyl) pyrimidines in the presence of tin (IV) chloride gave the β-nucleosides as major products in good yields. Thus, the reaction of 12 with silylated thymine gave the thymidine derivative 24, with β:α ratio of ~4:1. Condensation of 12 with the silylated uracil and N$^4$-benzoylcytosine gave the corresponding nucleosides 25 and 26, respectively, with β:α ratio of ~9:1 in both reactions. Treatment of 24–26 with boron trichloride afforded the pyrimidine bicyclonucleosides 27–29, respectively. In the case of cytidine derivative, the benzoyl group of 29 was removed by treatment with ammonia to give 30. An alternative route (not shown) to prepare 30 started from 28, which was acetylated at O3' and O5', followed by the reaction with triazole and the subsequent treatment with ammonia. In this way, 30 was obtained in moderate yield.

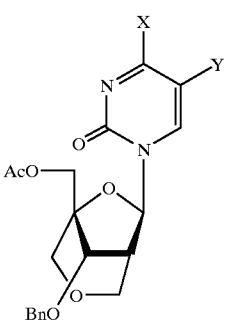 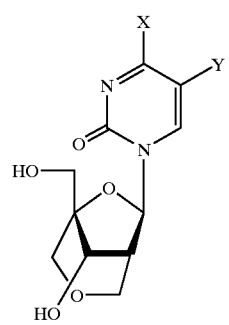

24 X = OH Y = Me
25 X = OH, Y = H
26 X = NHBz, Y = H

27 X = OH Y = Me
28 X = OH, Y = H
29 X = NHBz, Y = H
30 X = NH$_2$, Y = H

The condensation of 12 with the silylated purines, along with tin (IV) chloride as the coupling reagent, was also investigated. Unlike the reactions with pyrimidines, the condensation of the silylated 6-chloropurine with 12 yielded not only the α- and β-nucleosides 16 and 17, but also an N$^7$-coupling product (not shown). Similarly, the condensation of the silylated N$^2$-acetyl-guanine with 12 yielded a mixture of three products, the N$^7$-coupled β-nucleoside 31 (42%), the desired β-nucleoside 32 (10%) and the α-nucleoside 22 (6%). However, when heated with the silylated N²-acetylguanine in the presence of trimethylsilyl triflate, the N⁷-coupled product 31 was partially converted to the N⁹-coupled, α- and β-bicyclonucleosides 22 (~22%) and 32 (~25%). The separated 32 was subjected to the same treatments as 22 to give the bicyclic β-guanosine 33.

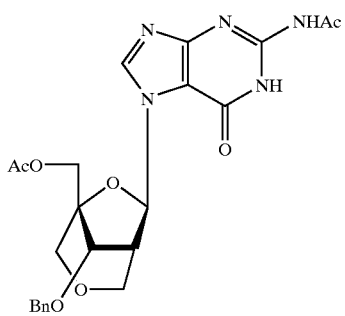

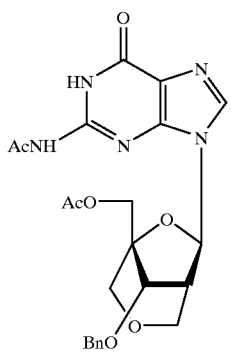

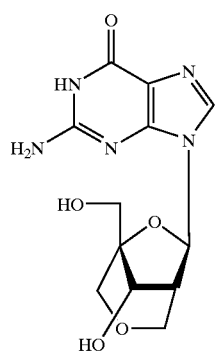

Stereochemical assignments of the 2,6-dioxabicyclo[3,2,1]octane derivative 11 and the bicyclonucleosides formed from condensation of bicyclic sugars with silylated nucleoside bases can be assigned by NOE proton NMR. As indicated by a stick-ball model, the rigid dioxabicyclo[3,2,1]octane ring system forces the protons (H1' and H2') at C1' and C2' of the α-bicyclonucleosides to become nearly parallel, whereas the H1' and H2' in the β-bicyclonucleosides direct to the opposite sides. For example, the torsion angle of H1'-C1'-C2'-H2' of the bicyclic α-thymidine 15 after a geometry optimization is 37° and, in consistency with this, a coupling constant of 3.9 Hz in proton NMR was observed. The torsion angle of H1'-C1'-C2'-H2' in the bicyclic β-thymidine 27 is 96° after a geometry optimization and, as expected, no coupling between the H1' and H2' was observed. In fact, the proton at C1' in all the β-bicyclonucleosides measured is a single peak. In contrast, in all the α-bicyclonucleosides measured the proton at C1' is a doublet with a coupling constant of ~4.0 Hz.

The stereochemical assignments of the bicyclonucleosides were further confirmed by X-ray crystal structures of the bicyclic thymidines 15 and 27. The ribose ring of the dioxabicyclo[3,2,1]octane sugar moiety in both compounds adopts a typical C3'-endo sugar pucker while the six-membered ring in the sugar moiety adopts the chair form. The thymine base in both compounds has the anti orientation.

Uses of Contemplated Compounds

It is generally contemplated that the nucleosides according to the inventive subject matter will have numerous biological activities, and especially contemplated biological activities include in vitro and in vivo inhibition of DNA and/or RNA polymerases, reverse transcriptases, and ligases. Preliminary experiments using HCV RNA-dependent RNA polymerase (data not shown) indicate that contemplated compounds may act as inhibitors of the polymerase, and may even be employed as substrates in the formation of a nascent polynucleotide.

Therefore, contemplated nucleosides will exhibit particular usefulness as an in vitro and/or in vivo antiviral agent, antineoplastic agent, or immunomodulatory agent. Particularly contemplated antiviral activities include at least partial reduction of viral titers of respiratory syncytial virus (RSV), hepatitis B virus (HBV), hepatitis C virus (HCV), herpes simplex type 1 and 2, herpes genitalis, herpes keratitis, herpes encephalitis, herpes zoster, human immunodeficiency virus (HIV), influenza A virus, Hanta virus (hemorrhagic fever), human papilloma virus (HPV), and measles virus. Consequently, a method of treating a viral disease may include a step in which contemplated compounds are provided. In a further step, the compound is administered at a dosage effective to reduce viral propagation (i.e., at least one of viral replication, polyprotein processing, viral peptide assembly, budding from an infected cell, and entry into a cell). Particularly contemplated viral infections include infection with the hepatitis C virus.

In further contemplated aspects, and especially where the compounds according to the inventive subject matter are employed as therapeutic agents for treatment of an HCV infection, it should be recognized that contemplated compounds may be administered together with additional pharmacologically active molecules. Among various such additional molecules, especially preferred molecules include antiviral small-molecule drugs (e.g., nucleoside analogs) and cytokines (particularly an interferon, and most particularly interferon alpha or interferon gamma). Administration will preferably be in the form of a pharmaceutical composition comprising contemplated compounds and a pharmaceutically acceptable carrier (see below).

While it is generally contemplated that such compounds will exhibit a direct antiviral effect (i.e., inhibit the viral polymerase), it is also contemplated that such compounds may also have an indirect antiviral effect (i.e., influence a host system to reduce viral propagation, to produce virus specific antibodies, or to eradicate virus-infected cells), for example, an immunomodulatory effect.

Especially contemplated immunomodulatory activity includes modulation of some portion of a mammal's immune system, and especially modulation of cytokine profiles of Type 1 and Type 2. Where modulation of Type 1 and Type 2 cytokines occurs, it is contemplated that the modulation may include suppression of both Type 1 and Type 2, suppression of Type 1 and stimulation of Type 2, or suppression of Type 2 and stimulation of Type 1.

Where contemplated nucleosides are administered in a pharmacological composition, it is contemplated that suitable nucleosides can be formulated in admixture with a pharmaceutically acceptable carrier. For example, contemplated nucleosides can be administered orally as pharmacologically acceptable salts, or intravenously in physiological saline solution (e.g., buffered to a pH of about 7.2 to 7.5). Conventional buffers such as phosphates, bicarbonates or citrates can be used for this purpose. Of course, one of ordinary skill in the art may modify the formulations within the teachings of the specification to provide numerous formulations for a particular route of administration. In particular, contemplated nucleosides may be modified to render them more soluble in water or other vehicle, which for example, may be easily accomplished by minor modifications (salt formulation, esterification, etc.) that are well within the ordinary skill in the art. It is also well within the ordinary skill of the art to modify the route of administration and dosage regimen of a particular compound in order to manage the pharmacokinetics of the present compounds for maximum beneficial effect in a patient.

In certain pharmaceutical dosage forms, prodrug forms of contemplated nucleosides may be formed for various purposes, including reduction of toxicity, increasing the organ- or target cell specificity, etc. Among various prodrug forms, acylated (acetylated or other) derivatives, pyridine esters and various salt forms of the present compounds are preferred. Alternatively, or additionally, preferred prodrugs will comprise an ester (e.g., phosphate or phosphonate ester) with at least one of the $R_2$ or $R_3$ group of contemplated compounds (e.g., where $R_2$ and/or $R_3$ are OH). Contemplated prodrugs will advantageously reduce cytotoxicity, increase specificity towards a target organ (e.g., liver), and/or increase bioavailability. One of ordinary skill in the art will recognize how to readily modify the present compounds to pro-drug forms to facilitate delivery of active compounds to a target site within the host organism or patient. One of ordinary skill in the art will also take advantage of favorable phannacokinetic parameters of the pro-drug forms, where applicable, in delivering the present compounds to a targeted site within the host organism or patient to maximize the intended effect of the compound.

In addition, contemplated compounds may be administered alone or in combination with other agents for the treatment of various diseases or conditions. Combination therapies according to the present invention comprise the administration of at least one compound of the present invention or a functional derivative thereof and at least one other pharmaceutically active ingredient. The active ingredient(s) and pharmaceutically active agents may be administered separately or together and when administered separately this may occur simultaneously or separately in any order. The amounts of the active ingredient(s) and pharmaceutically active agent(s) and the relative timings of administration will be selected in order to achieve the desired combined therapeutic effect.

EXAMPLES

The synthetic approaches utilized to prepare the compounds described can also be used to synthesize other claimed compounds. The present invention includes, but is not limited to the compounds prepared through the following examples. The numbers in parenthesis following the compound names in the examples correspond to the numbers of the structures in the detailed description section.

Example 1

Preparation of 1-α-methyl-3,5-O-(1,1,3,3-tetraisopropyl-1,3-disiloxanediyl)-D-ribofuranose (2)

α-Methylarabinose was prepared according to a published procedure (Tejima, S.; Fletcher, Jr. H. G. *J. Org. Chem.* 1963, 28. 2999–3003) and separated from its β-anomer (a minor product) through chromatography on silica. To a stirred solution of α-methylarabinose (19.27 g, 119.9 mmol) in anhydrous pyridine (200 mL) at 0° C. was added 1,3-dichloro-1,1,3,3-tetraisopropyldisiloxane (38.4 mL, 119.9 mmol). The resulting solution was stirred at 0° C. for 1 h and then at room temperature for 1.5 h. The solution was cooled to 0° C. and water (20 mL) added. The mixture was stirred for 10 min and diluted with EtOAc. The aqueous layer was extracted with EtOAc. The combined organic layer was dried ($Na_2SO_4$), and concentrated to dryness. Chromatography on silica with 15% EtOAc in hexanes gave 42.7 g (88%) of the titled compound as a colorless syrup.

Example 2

Preparation of 2-C,2-O-didehydro-α-methyl-3,5-O-(1,1,3,3-tetraisopropyl-1,3-disiloxanediyl)-D-ribofuranose (3)

To a stirred solution of 1-α-methyl-3,5-O-(1,1,3,3-tetraisopropyl-1,3-disiloxane-diyl)-D-ribofuranose (42.6 g, 104.9 mmol) and DCC (43.4 g, 209.8 mmol) in anhydrous DMSO (250 mL) and ether (100 mL) at 0° C. under argon was added a solution of trifluoroacetic acid (4.04 mL, 52.5 mmol) and pyridine (8.44 mL, 105 mmol) in DMSO (30 mL). The resulting reaction mixture was warmed to room temperature, stirred for 5 h, and then cooled to 0° C. Oxalic acid (21.3 g, 236 mmol) in methanol (60 mL) was added, followed by addition of water (30 mL). The resulting mixture was stirred at room temperature for 1 h and the precipitate was filtered and washed thoroughly with hexanes. The filtrate was further diluted with hexanes, washed with water five times, dried ($Na_2SO_4$), and concentrated to dryness. Chromatography on silica with 2% MeOH in methylene chloride-hexanes (1:2) gave 37.6 g (89%) of the titled compound as a colorless syrup; $^1$H NMR (CDCl$_3$) δ 1.00–1.12 (m, 28H, TIPDS), 3.47 (s, 3H, OCH$_3$), 4.05–4.19 (m, 3H, H4, H5a, H5b), 4.51 (dd, J=9.3 Hz, 1.5 Hz, 1H, H3), 4.89 (t, J 1.5 Hz, 1H, H1).

Example 3

Preparation of 2-deoxy-2-methylene-1-α-methyl-3,5-O-(1,1,3,3-tetraisopropyl-1,3-disiloxanediyl)-D-ribofuranose To a stirred suspension of methyltriphenylphosphonium bromide (21.5 g, 60.1 mmol) in anhydrous ether (1380 mL)

at room temperature under argon was added a solution of sodium t-pentoxide (5.97 g, 54.0 mmol) in anhydrous benzene (50 mL). The resulting light-yellow mixture was stirred at room temperature for 6 h and cooled to −10° C., then a solution of 2-C, 2-O-didehydro-α-methyl-3,5-O-(1,1,3,3-tetraisopropyl-1,3-disiloxanediyl)-D-ribofuranose (12.1 g, 30.1 mmol) in ether (35 mL) was added. The reaction mixture was stirred at −10° C. for 1 h, washed with brine twice, dried ($Na_2SO_4$), and concentrated. Chromatography on silica with 5% EtOAc in hexanes gave 11.0 g (91%) of the titled compound as a colorless syrup; $^1$H NMR ($CDCl_3$) δ 1.00–1.12 (m, 28H, TIPDS), 3.45 (s, 3H, $OCH_3$), 3.73 (dt, J=9.0 Hz, 3.0 Hz, 1H, H4), 4.02, 4.03 (2s, 2H, H5), 4.62 (dt, J=9.0 Hz, 2.7 Hz, 1H, H3), 5.27 (m, 1H, H1), 5.32–5.36 (m, 2H, H2').

Example 4

Preparation of 2-deoxy-2-methylene-1-α-methyl-D-ribofuranose (4)

To a stirred solution of 2-deoxy-2-methylene-1-α-methyl-3,5-O-(1,1,3,3-tetraiso-propyl-1,3-disiloxanediyl)-D-ribofuranose (35.0 g, 87.1 mmol) in THF (200 mL) was added 1.0 M TBAF in THF (180 mL). The resulting solution stood at room temperature for 1 h. THF was evaporated and the residue chromatographed on silica with 10% EtOH in methylene chloride to give 14.6 g (88%) of the titled compound as a syrup.

Example 5

Preparation of 3-O-benzyl-5-O-(t-butyldimethylsilyl)-2-deoxy-2-methylene-1-α-methyl-D-ribofuranose (5)

A solution of 2-deoxy-2-methylene-1-a-methyl-D-ribofuranose (13.7 g, 85.5 mmol) and -TBDMS-Cl (13.5 g, 89.6 mmol) in anhydrous pyridine (130 mL) stood at room temperature for 15 h. After cooling to 0° C. and addition of water (2 mL), the resulting mixture was stirred at room temperature for 1 h, concentrated to half the volume, diluted with EtOAc, washed with brine, dried ($Na_2SO_4$), and concentrated to dryness. The thoroughly dried crude was dissolved in THF (70 mL) and added to a stirred mixture of NaH (60% in mineral oil, 5.6 g, 140 mmol) in THF (350 mL) at 0° C. After stirring at room temperature for 40 min, benzyl bromide (10.75 mL, 90.5 mmol) was added. The reaction mixture was stirred for 4 h and cooled to 0° C., followed by slow addition of water (2 mL) and then 10% AcOH in water until pH 7. The mixture was diluted with EtOAc, washed with brine, then with dilute sodium bicarbonate, dried ($Na_2SO_4$), and concentrated to dryness. Chromatography on silica with 0–10% EtOAc in hexanes gave 23.8 g (76%) of the titled compound as a colorless liquid; $^1$H NMR ($CDCl_3$) δ 0.01 (s, 3H, $SiCH_3$), 0.02 (s, 3H, $SiCH_3$), 0.85 (s, 9H, t-Bu), 3.41 (s, 3H, $OCH_3$), 3.60–3.72 (m, 2H, H5a, H5b), 4.20 (dd, J=8.7 Hz, 4.5 Hz, 1H, H3), 4.57, 4.66 (AB, J=12.0 Hz, 2H, Bn), 5.22 (t, J=1.2 Hz, 1H, H1), 5.38 (t, J=1.5 Hz, 1H, H2a'), 5.43 (m, J=1.2 Hz, 1H, H2b'), 7.23–7.37 (m, 5H, Bn); Anal. Calcd. for $C_{20}H_{32}O_4Si$: C, 65.89; H, 8.85. Found: C, 65.92; H, 9.22.

Example 6

Preparation of 3-O-Benzyl-5-0-(t-butyldimethylsilyl)-2-deoxy-2-hydroxymethyl-1-α-methyl-D-ribofuranose (6)

To a stirred solution of 3-O-benzyl-5-O-(t-butyldimethylsilyl)-2-deoxy-2-methylene-1-α-methyl-D-ribofuranose (5.28 g, 14.50 mmol) under argon was added 9-BBN (0.5 M in THF, 87 mL). The resulting solution was stirred at ambient temperature for 1 h, then at 40° C. overnight, cooled to room temperature, and transferred to a flask containing sodium perborate tetrahydrate (13.39 g, 87 mmol) in water (85 mL) and ethanol (85 mL). The resulting mixture was vigorously stirred at 50° C. for 4 h, cooled to 0° C., neutralized with AcOH to pH 8, and concentrated to a small volume. The remaining volume was diluted with water (20 mL) and extracted with methylene chloride three times. The combined organic layer was washed with brine twice, dried ($Na_2SO_4$), and concentrated to dryness. Chromatography on silica with EtOAc-hexanes (1:2) gave 5.17 g (93%) of the titled compound as a colorless syrup; $^1$H NMR ($CDCl_3$) δ 0.03 (s, 6H, $SiCH_3$), 0.87 (s, 9H, t-butyl), 2.34–2.43 (m, 1H, H2), 3.39 (s, 3H, $OCH_3$), 3.48 (dd, J=10.5 Hz, 6.0 Hz, 1H, H5a), 3.60 (dd, J=10.5 Hz, 3.6 Hz, 1H, H5b), 3.88 (d, J=7.2 Hz, 2H, H2'), 3.98 (dd, J=7.2 Hz, 2.7 Hz, 1H, H3), 4.17 (m, 1H, H4), 4.44, 4.66 (AB, J=12.3 Hz, 2H, Bn), 4.95 (d, J=5.4 Hz, 1H, H1), 7.23–7.36 (m, 5H, Bn); Anal. Calcd. for $C_{20}H_{34}O_5Si$: C, 62.79; H, 8.96. Found: C, 62.92; H, 9.21.

Example 7

Preparation of 3-O-benzyl-2-deoxy-2-(4,4'-dimethoxytrityloxymethyl)-1-α-methyl-D-ribofuranose (7)

A solution of 3-O-benzyl-5-O-(t-butyldimethylsilyl)-2-deoxy-2-hydroxymethyl-1-α-methyl-D-ribofuranose (6.60 g, 17.28 mmol) and DMT-Cl (7.03 g, 20.74 mmol) in anhydrous pyridine (50 mL) stood at room temperature overnight and the reaction was quenched by adding water (8 mL). The resulting solution stood for 10 min and was diluted with EtOAc, washed with brine three times, dried ($Na_2SO_4$), and concentrated to give the crude 9, which was dissolved in THF (52 mL). TBAF (1.0 M in THF, 26 mL) was added and the resulting solution stood at room temperature for 30 min. THF was evaporated and the residue chromatographed on silica with EtOAc-hexane (1:1) to give 9.28 g (94%) of the titled compound as a white foam; $^1$H NMR ($CDCl_3$) δ 2.33–2.42 (m, 1H, H2), 3.26–3.63 (m, 7H, H5a, H5b, H2a', H2b', $OCH_3$), 3.79 (d, J=1.2 Hz, 6H, DMT), 3.91 (dd, J=7.5 Hz, 2.4 Hz, 1H, H3), 4.13 (m, 1H, H4), 4.41, 4.50 (AB, J=12.9 Hz, 2H, Bn), 5.05 (d, J=5.1 Hz, 1H, H1), 6.78–6.85 (m, 4H, DMT), 7.14–7.47 (m, 14H, Bn, DMT); Anal. Calcd. for $C_{35}H_{38}O_7$: C, 73.66; H, 6.71. Found: C, 73.57; H, 6.76.

Example 8

Preparation of 3-O-benzyl-2-deoxy-2-(4, 4'-dimethoxytrityloxymethyl)-5-C, 5-O-didehydro-1-α-methyl-D-ribofuranose (8)

To a stirred solution of 3-O-benzyl-2-deoxy-2-(4,4'-dimethoxytrityloxymethyl)-1-α-methyl-D-ribofuranose (9.18 g, 16.16 mmol) and DCC (10.0 g, 48.49 mmol) in anhydrous DMSO (60 mL) at 10° C. was added a solution of trifluoroacetic acid (0.622 mL, 8.08 mmol) and pyridine (1.95 mL, 24.24 mmol) in DMSO (15 mL). The resulting reaction mixture was stirred at 10° C. for 1 h, at room temperature for 6 h, and then cooled to 0° C. After addition of water (8 mL), the mixture was stirred overnight and diluted with EtOAC. The precipitate was filtered and thoroughly washed with EtOAc. The combined filtrate was washed with brine five times, dried ($Na_2SO_4$), and concentrated to dryness. Chromatography on silica with EtOAc-hexanes (1:1) gave 8.26 g (90%) of the titled compound as a white foam.

Example 9

Preparation of 3-O-benzyl-2-deoxy-2-(4, 4'-dimethoxytrityloxymethyl)-4-C-hydroxymethyl-1-α-methyl-D-ribofuranose (9)

To a stirred solution of 3-O-benzyl-2-deoxy-2-(4,4'-dimethoxytrityloxymethyl)-5-C,5-O-didehydro-1-α-methyl-D-ribofu-ranose (8.0 g, 14.08 mmol) and formaldehyde (37% in water, 85 mL) in dioxane (420 mL) at 0° C. was added dropwise an aqueous NaOH solution (2.0 M, 210 mL) during 15 min. The resulting cloudy solution was stirred at room temperature for 2 days to become a clear solution. After cooling to 0° C., the solution was neutralized with 10% acetic acid to pH 8, concentrated to a small volume, diluted with water (100 mL), and extracted with methylene chloride three times. The combined organic layer was washed with brine, dried ($Na_2SO_4$), and concentrated to dryness. Chromatography on silica with 4–5% ethanol in methylene chloride gave 8.11 g (94%) of the titled compound as a white foam; $^1H$ NMR ($CDCl_3$) δ 2.46–2.57 (m, 1H, H2), 3.23–3.73 (m, 9H, H5, H4', H2', $OCH_3$), 3.79 (d, J=1.8 Hz, 6H, DMT), 4.14 (d, J=6.9 Hz, 1H, H3), 4.43, 4.47 (AB, J=12 Hz, 2H, Bn), 4.97 (d, J=4.8 Hz, 1H, H1), 6.77–6.85 (m, 4H, DMT), 7.11–7.46 (m, 14H, Bn, DMT).

Example 10

Preparation of 3-O-benzyl-2-deoxy-2-hydroxymethyl-5-O-mesyl-4-mesyloxymethyl-1-α-methyl-D-ribofuranose (10)

To a stirred solution of 3-O-benzyl-2-deoxy-2-(4,4'-dimethoxytrityloxymethyl)-4-C-hydroxymethyl-1-α-methyl-D-ribofu-ranose (7.80 g, 13.0 mmol) in anhydrous pyridine (60 mL) at 0° C. under argon was added dropwise methanesulfonyl chloride (3.03 mL, 39 mmol). The resulting reaction mixture was stirred at room temperature for 45 min, cooled to 0° C., and diluted by adding water (5 mL). The resulting mixture was stirred at room temperature for 15 min, diluted with EtOAc, washed with brine three times, dried ($Na_2SO_4$), and concentrated to give the crude as a white foam, which was dissolved in AcOH-Water (80:20, 400 mL). The resulting solution stood at room temperature for 2 h and was diluted with water (200 mL), and concentrated to about a quarter of the volume. Water (100 mL) was added and the mixture concentrated to dryness. Chromatography on silica with EtOAc-hexanes (3:1 to 1:0) gave 5.32 g (90%) of the titled compound as a semi-solid; $^1H$ NMR ($CDCl_3$) δ 2.43–2.54 (m, 1H, H2), 3.01 (s, 3H, OMs), 3.03 (s, 3H, OMs), 3.41 (s, 3H, $OCH_3$), 3.81 (d, J=4.8 Hz, 2H, H2'), 4.01, 4.04 (AB, J=10.5 Hz, 2H, H4'), 4.21 (d, J=7.5 Hz, 1H, H3), 4.30, 4.50 (AB, J=1.8 Hz, 2H, H5), 4.56, 4.63 (AB, J=12.0 Hz, 2H, Bn), 4.99 (d, J=5.1 Hz, 1H, H1), 7.30–7.42 (m, 5H, Bn); Anal. Calcd. for $C_{17}H_{27}O_{10}S_2$: C, 44.82; H, 5.97. Found: C, 44.68; H, 6.00.

Example 11

Preparation of (1S,3S,4R, 8S)-8-benzyloxy-1-hydroxymethyl-3-methoxy-2,6-dioxabicyclo[3,2,1]octane (11)

To a stirred mixture of NaH (60% in mineral oil, 1.83 g, 22.90 mmol) in anhydrous THF (200 mL) was added a solution of 3-O-benzyl-2-deoxy-2-hydroxymethyl-5-O-mesyl-4-mesyloxymethyl-1-α-methyl-D-ribofuranose (5.20 g, 11.45 mmol) in THF (30 mL). The resulting reaction mixture was stirred at 55° C. for 42 h and the reaction quenched by adding water at 0° C. THF was evaporated and an aqueous NaOH (0.5 M, 250 mL) added. The resulting mixture was heated at reflux for 24 h, cooled to 0° C., neutralized with dilute hydrochloric acid to pH 8, extracted with methylene chloride four times. The combined organic layer was dried ($Na_2SO_4$) and concentrated to dryness. Chromatography on silica with EtOAc-hexanes (2:1 to 1:0) gave 3.16 g (98%) of the titled compound as a colorless syrup; $^1H$ NMR ($CDCl_3$) δ 2.32 (m, 1H, H2), 3.41 (d, J=11.4 Hz, 1H, H4a'), 3.46–3.60 (m, 2H, 5H, H5, $OCH_3$), 3.91 (d, J=11.1 Hz, 1H, H4b'), 3.92 (dd, J=10.8 Hz, 2.4 Hz, 1H, H2a'), 4.01 (d, J=5.4 Hz, 1H, H3), 4.04 (d, J=10.5 Hz, 1H, H2b'), 4.58, 4.64 (AB, J=12.0 Hz, Bn), 5.07 (d, J=3.9 Hz, 1H, H1), 7.28–7.40 (m, 5H, Bn).

Example 12

Preparation of (1R, 3S,4R, 8S)-1-acetoxymethyl-8-benzyloxy-3-methoxy-2,6-dioxabicyclo[3,2,1]octane (12)

A solution of (1S,3S,4R,8S)-8-benzyloxy-1-hydroxymethyl-3-methoxy-2,6-dioxabicyclo[3,2,1]octane (1.60 g, 5.71 mmol), acetic anhydride (1.08 mL, 11.42 mmol), and DMAP (2.09 g, 17.13 mmol) in anhydrous methylene chloride (10 mL) was stirred at room temperature for 2 h, cooled to 0° C., and diluted with methanol (4 mL). The mixture was stirred at room temperature for 15 min, diluted with methylene chloride, washed with brine and then with 10% $NaHCO_3$, dried ($Na_2SO_4$), and concentrated to dryness. Chromatography on silica with ethyl acetate-hexanes (1:1) gave 1.82 g (99%) of the titled compound as a colorless syrup; 1H NMR ($CDCl_3$) δ 2.02 (s, 3H, OAc), 2.33 (m, 1H, H2), 3.50 (d, J=10.8 Hz, 1H, H4a'), 3.57 (s, 3H, $OCH_3$), 3.86–4.04 (m, 5H, H2a', H2b', H3, H4b', H5a), 4.14 (d, J=12.0 Hz, 1H, H5b), 4.50, 4.64 (AB, J=12.0 Hz, 1H, Bn), 5.09 (d, J=3.9 Hz, 1H, H1), 7.29–7.42 (m, 5H, Bn); Anal. Calcd. for $C_{17}H_{22}O_6$: C, 63.34; H, 6.88. Found: C, 63.41; H, 6.94.

Example 13

Preparation of (1R, 3S,4R,8S)-3-acetoxy-1-acetoxymethyl-8-benzyloxy-2,6-dioxabicyclo[3,2,1]octane (13)

To a stirred solution of (1S,3S,4R,8S)-8-benzyloxy-1-hydroxymethyl-3-methoxy-2,6-dioxabicyclo[3,2,1]octane (600 mg, 2.14 mmol) in a mixture of acetic acid (6.0 mL) and acetic anhydride (0.6 mL) at 0° C. was added dropwise concentrated sulfuric acid (57 μL, 1.07 mmol). The resulting reaction mixture was stirred at 0° C. for 10 min and then at room temperature for 2 h. After cooling to 0° C., the solution was diluted with EtOAc, washed with brine three times and then with 10% sodium bicarbonate, dried ($Na_2SO_4$), and concentrated to dryness. Chromatography on silica with EtOAc-hexanes (2:3) gave 696 mg (93%) of the titled compound (α-anomer) and 31 mg (3%) of the α-anomer, both as a colorless syrup. The β-anomer was solidified after standing at room temperature for days; m.p. 55–58° C.; $^1H$ NMR (CDCl$_3$) δ 2.03 (s, 3H, OAc), 2.08 (s, 3H, OAc), 2.36–2.39 (m, 1H, H2), 3.49 (d, J=10.8 Hz, H4a'), 3.73 (d, J=11.1 Hz, 2.7 Hz, 1H, H2a'), 3.89 (d, J=11.1 Hz, 1H, H4b'), 4.01 (d, J=11.1 Hz, 1H, H2b'), 4.03 (d, J=9.3 Hz, 1H, H5a'), 4.14 (d, J=5.1 Hz, 1H, H3), 4.55 (d, J=9.6 Hz, 1H, H5b), 4.55, 4.64 (AB, J=11.7 Hz, 2H, Bn), 6.39 (s, 1H, H1), 7.29–7.42 (m, 5H, Bn); Anal. Calcd. for C$_{18}$H$_{22}$O$_7$: C, 61.70; H, 6.33. Found: C, 61.74; H, 6.46.

Example 14

Preparation of (1R, 3S,4R, 8S)-1-acetoxymethyl-8-benzyloxy-3-(thymin-1-yl)-2,6-dioxabicyclo[3,2,1]octane (14)

A mixture of thymine (189 mg, 1.5 mmol) and anhydrous ammonium sulfate (15 mg) in HMDS (6 mL) was heated at reflux overnight. After removal of HMDS, the residue was co-evaporated with anhydrous m-xylene, dried under vacuum for 30 min, and dissolved in a solution of (1R, 3S,4R,8S)-3-acetoxy-1-acetoxymethyl-8-benzyloxy-2,6-dioxabicyclo[3,2,1]octane (306 mg, 0.87 mmol) in 1,2-dichloroethane (5 mL). To this stirred solution under argon was added dropwise trimethylsilyl triflate (0.38 mL) in 1,2-dichloroethane (2 mL). The resulting solution was heated under reflux for 2 h, cooled to 0° C., diluted with chloroform, and neutralized with 10% NaHCO$_3$ (10 mL). The organic layer was separated and the aqueous layer extracted with chloroform twice. The combined organic layer was dried (Na$_2$SO$_4$) and concentrated to dryness. Crystallization from EtOAc-CH$_2$Cl$_2$ gave the titled compound (303 mg, 83%) as a colorless solid; m.p. 198–200° C.; $^1$H NMR (CDCl$_3$) δ 1.94 (d, J=1.2 Hz, 1H, ArCH$_3$), 2.04 (s, 3H, OAc), 2.93 (m, 1H, H2'), 3.50 (dd, J=11.8 Hz, 2.1 Hz, 1H, H2a"), 3.59 (d, J=11.4 Hz, 1H, H4a"), 4.016 (d, J=11.7 Hz, 1H, H4b")), 4.022 (d, J=12.6 Hz, 1H, H5a'), 4.09 (d, J=12.0 Hz, 1H, H2b"), 4.11 (d, J=4.5 Hz, 1H, H3'), 4.27 (d, J=12.6 Hz, 1H, H5b'), 4.53, 4.70 (AB, J=11.7 Hz, 2H, Bn), 5.88 (d, J=3.6 Hz, 1H, H1'), 7.30–7.42 (m, 5H, Bn), 7.74 (d, J=1.5 Hz, 1H, H6), 8.79 (s, 1H, NH); Anal. Calcd. for C$_{21}$H$_{24}$N$_2$O$_7$: C, 60.57; H, 5.81; N, 6.73. Found: C, 60.55; H, 5.84; N, 6.69.

Example 15

Preparation of (1S,3S,4R,8S)-8-hydroxy-1-hydroxymethyl-3-(thymin-1-yl)-2, 6-dioxabicyclo[3,2,1]octane (15)

To a solution of (1R,3S,4R,8S)-1-acetoxymethyl-8-benzyloxy-3-(thymin-1-yl)-2,6-dioxabicyclo[3,2,1]octane in anhydrous methylene chloride (3 mL) at 10° C. was added boron trichloride (1.0 M in CH$_2$Cl$_2$, 6 mL). The resulting reaction mixture was stirred at 15° C. to room temperature overnight and cooled to 0° C. Methanol (1.5 mL) was added dropwise and the resulting mixture stirred at 0° C. for 15 min, followed by addition of triethylamine (2 mL). The solvent was evaporated and the precipitate thoroughly extracted with warm acetone. The acetone solution was dried (Na$_2$SO$_4$) and concentrated to dryness. Chromatography on silica with 10% methanol in chloroform gave 99 mg of 20 as a white foam. Crystallization from acetone gave 95 mg (93%) of the titled compound as a colorless solid; m.p. 225–226° C.; $^1$H NMR (DMSO-d$_6$) δ 1.76 (d, J=0.9 Hz, 1H, ArCH$_3$), 2.45 (m, 1H, H2'), 3.25 (dd, J=11.4 Hz, 2.1 Hz, 1H, H2a"), 3.32–3.52 (m, 2H, H5'), 3.53 (d, J=11.4 Hz, 1H, H4a"), 3.72 (d, J=11.1 Hz, 1H, H4b"), 3.93 (d, J=11.1 Hz, 1H, H2b"), 4.16 (m, 1H, H3'), 4.84 (t, J=6.0 Hz, 1H, OH), 5.74 (d, J=4.2 Hz, 1H, H1'), 5.84 (d, J=3.9 Hz, 1H, OH), 7.76 (d, J=1.2 Hz, 1H, H6), 11.32 (s, 1H, NH); MS m/z 285 (MH$^+$); Anal. Calcd. for C$_{12}$H$_{16}$N$_2$O$_6$: C, 50.70; H, 5.67; N, 9.85. Found: C, 50.85; H, 5.68; N, 9.75.

Example 16

Preparation of (1R,3R,4R,8S)-1-acetoxymethyl-8-benzyloxy-3-(6-chloropurin-9-yl)-2,6-dioxabicyclo[3,2,1]octane (17) and (1R,3S,4R,8S)-1-acetoxymethyl-8-benzyloxy-3-(6-chloropurin-9-yl)-2,6-dioxabicyclo[3,2,1]-octane (16)

A mixture of 6-chloropurine (246 mg, 1.6 mmol) and HMDS (8.0 mL) was refluxed under argon for 2 h. HMDS was evaporated and the residue dried under vacuum for 30 min and then dissolved in a solution of (1R,3S,4R,8S)-3-acetoxy-1-acetoxymethyl-8-benzyloxy-2,6-dioxabicyclo[3,2,1]octane (302 mg, 0.83 mmol) in anhydrous 1,2-dichloroethane (5.0 mL), followed by addition of trimethylsilyl triflate (0.38 mL, 2.25 mmol) in 1,2-dichloroethane (2.0 mL). The resulting solution was heated at reflux under argon for 45 min. The work up was the same as that described before. Chromatography on silica with EtOAc-hexanes (1:1) gave (1R,3S,4R,8S)-1-acetoxymethyl-8-benzyloxy-3-(6-chloropurin-9-yl)-2,6-dioxabicyclo[3,2,1]-octane (122 mg, α-anomer) and (1R, 3R,4R,8S)-1-acetoxymethyl-8-benzyloxy-3-(6-chloropurin-9-yl)-2,6-dioxabicyclo-[3,2,1]octane (157 mg, β-anomer), both as a colorless solid. Total yield was 75%. The α-isomer: $^1$H NMR (CDCl$_3$) δ 2.05 (s, 3H, OAc), 2.89 (m, 1H, H2'), 3.23 (dd, J=12.0 Hz, 2.4 Hz, 1H, H2a"), 3.72 (d, J=11.7 Hz, H4a"), 4.09 (d, J=12.3 Hz, 2H, H4", H5a'), 4.13 (d, J=13.2 Hz, 1H, H2b"), 4.24 (d, J=4.8 Hz, H3'), 4.29 (d, J=12.3 Hz, 1H, H5b'), 4.60, 4.74 (AB, J=11.7 Hz, 2H, Bn), 6.50 (d, J=4.2 Hz, 1H, H1'), 7.32–7.44 (m, 5H, Bn), 8.69 (s, 1H, H8), 8.78 (s, 1H, H2). The β-isomer: m.p. 124–125° C. (EtOAc-hexanes); $^1$H NMR (CDCl$_3$) δ 2.05 (s, 3H, OAc), 2.90 (m, 1H, H2'), 3.55 (d, J=11.1 Hz, H4a"), 3.95–4.03 (m, 2H, H2a", H4b"), 4.18–4.24 (m, 3H, H5', H2b"), 4.32 (d, J=4.8 Hz, H3'), 4.47, 4.63 (AB, J=11.7 Hz, 2H, Bn), 6.52 (s, 1H, H1'), 7.24–7.35 (m, 5H, Bn), 8.40 (s, 1H, H8), 8.72 (s, 1H, H2); Anal. Calcd. for C$_{21}$H$_{21}$N$_4$O$_5$Cl: C, 56.70; H, 4.76; N, 12.59. Found: C, 56.36; H, 4.56; N, 12.37.

Example 17

Preparation of (1R,3S,4R,8S)-1-acetoxymethyl-3-(N$^2$-acetylguanin-9-yl)-8-benzyloxy-2,6-dioxabicyclo[3,2,1]octane (22)

A mixture of N$^2$-acetyl guanine (193 mg, 1.0 mmol) and ammonium sulfate (20 mg) in pyridine (1.0 mL) and HMDS (5.0 mL) was refluxed under argon for 3 h. The resulting clear solution was concentrated and co-evaporated with xylene (10 mL, sodium dried). The residue was dried under vacuum at 50° C. for 1 h and dissolved in a solution of (1R,3S,4R,8S)-3-acetoxy-1-acetoxymethyl-8-benzyloxy-2,6-dioxabicyclo[3,2,1]octane (175 mg, 0.5 mmol) in anhydrous 1,2-dichloroethane (5.0 mL), followed by addition of trimethylsilyl triflate (0.27 mL, 1.5 mmol) in 1,2-dichloroethane (1.0 mL). The resulting solution was stirred at room temperature under argon for 30 min, then heated at 70–75° C. for 2 h, cooled to 0° C., and neutralized with 10% sodium bicarbonate (10 mL). The resulting mixture was stirred for 15 min and the organic layer separated. The aqueous layer was extracted with chloroform twice. The combined organic layer was dried ($Na_2SO_4$) and concentrated to dryness. Chromatography on silica with 10% ethanol in $CHCl_3$-EtOAc (1:1) gave the titled compound (72 mg, 30%) as a colorless solid; m.p. 249° C. (decom., EtOAc); $^1$H NMR ($CDCl_3$) δ 2.01 (s, 3H, OAc), 2.29 (s, 3H, NAc), 2.75 (m, 1H, H2'), 3.29 (dd, J=11.7 Hz, 1.8 Hz, 1H, H2a"), 3.66 (d, J=11.4 Hz, 1H, H4a"), 4.03 (d, J=11.4 Hz, 1H, H4b"), 4.05 (d, J=11.7 Hz, 1H, H2b"), 4.70 (d, J=12.3 Hz, 1H, H5a'), 4.13 (d, J=4.8 Hz, H3'), 4.23 (d, J=12.3 Hz, 1H, H5b'), 4.53, 4.67 (AB, J=11.7 Hz, 2H, Bn), 6.17 (d, J=4.2 Hz, 1H, H1'), 7.28–7.40 (m, 5H, Bn), 8.32 (s, 1H, H8), 9.80 (s, 1H, NH), 12.12 (s, 1H, NH).

Example 18

Preparation of (1S,3R,4R,8S)-3-(adenin-9-yl)-8-hydroxy-1-hydroxymethyl-2,6-dioxabicyclo[3,2,1]octane (18)

A solution of (1R,3R,4R,8S)-1-acetoxymethyl-8-benzyloxy-3-(6-chloropurin-9-yl)-2,6-dioxabicyclo[3,2,1]-octane (100 mg, 0.225 mmol) in a mixture of dioxane (20 mL) and 30% aqueous ammonium hydroxide (20 mL) was heated in a steel bomb at 100° C. for 16 h. Solvents were evaporated and the residue was dissolved in methanol, followed by addition of 20% palladium hydroxide on charcoal (50% water, 3×250 mg, added each day). The hydrogenolysis was conducted at room temperature under 55 psi hydrogen for 4 days. The catalyst was filtered and washed with methanol. The combined methanol solution was concentrated and the residue chromatographed on silica with 20% methanol in methylene chloride to give the titled compound (39 mg, 59%) as a colorless solid, which was crystallized from methanol; m.p. 250° C. (decom.); $^1$H NMR (DMSO-$d_6$+$D_2O$): δ 2.53 (m, 1H, H2'), 3.33 (d, J=11.1 Hz, 1H, H2a"), 3.40 (d, J=12.3 Hz, 1H, H5a'), 3.50 (d, J=12.6 Hz, 1H, H5b'), 3.69–3.76 (m, 2H, H2b", H4a"), 4.05 (d, J=10.2 Hz, H4b"), 4.45 (d, J=5.1 Hz, 1H, H3'), 6.26 (s, 1H, H1'), 7.28 (m, 2H, $NH_2$), 8.12 (s, 1H, H8), 8.33 (s, 1H, H2); MS: 294 (MH$^+$); Anal. Calcd. for $Cl_2H_{15}N_5O_4$: C, 49.14; H, 5.16; N, 23.88. Found: C, 49.01; H, 4.97; N, 23.92.

Example 19

Preparation of (1S,3S,4R,8S)-3-(adenin-9-yl)-8-hydroxy-1-hydroxymethyl-2,6-dioxabicyclo[3,2,1]octane (19)

A similar procedure as described in Example 18 gave the titled compound (43 mg, 65%) as a colorless solid from (1R,3S,4R,8S)-1-acetoxymethyl-8-benzyloxy-3-(6-chloropurin-9-yl)-2,6-dioxabicyclo[3,2,1]octane (100 mg). $^1$H NMR ($CD_3OD$): δ 2.71 (m, 1H, H2'), 3.13 (dd, J=11.7 Hz, 2.4 Hz, 1H, H2a"), 3.57 (d, J=12.6 Hz, 1H, H5a'), 3.64 (d, J=11.1 Hz, H4a"), 3.68 (d, J=12.3 Hz, 1H, H5b'), 3.96 (d, J=11.1 Hz, 1H, H4b"), 4.14 (d, J=11.7 Hz, 1H, H2b"), 6.39 (d, J=4.2 Hz. 1H, H1'), 8.04 (s, 1H, H8), 8.44 (s, 1H, H2); MS m/z 294 (MH$^+$).

Example 20

Preparation of (1S,3R,4R,8S)-8-hydroxy-1-hydroxymethyl-3-(hypoxanthin-9-yl)-2,6-dioxabicyclo[3,2,1]octane (20)

To a solution of (1R,3R,4R,8S)-1-acetoxymethyl-8-benzyloxy-3-(6-chloropurin-9-yl)-2,6-dioxabicyclo[3,2,1]-octane (150 mg, 0.34 mmol) and mercaptoethanol (0.19 mL, 2.7 mmol) in methanol (20 mL) was added sodium methoxide (0.37 mL of 5.4 M in methanol, 2.0 mmol). The resulting solution was heated under reflux for 6 h, cooled to room temperature, neutralized with 10% AcOH to pH 7. Methanol was evaporated and the residue diluted with 1.0 M $NaHCO_3$ (15 mL), followed by extraction with 10% methanol in chloroform until the aqueous phase did not contain the product. The combined organic layer was dried ($Na_2SO_4$) and concentrated to dryness. Chromatography on silica with 10–15% methanol in chloroform gave 109 mg (84%) of the inosine derivative (not shown) as a colorless solid, 100 mg (0.26 mmol) of which was dissolved in methanol, followed by addition of 20% palladium hydroxide on charcoal (50% water, 600 mg). The hydrogenolysis was conducted at room temperature under 50 psi hydrogen for 3 days. The catalyst was filtered and washed with methanol. The combined methanol solution was concentrated and the residue chromatographed on silica with 20–25% methanol in methylene chloride to give 61 mg (61%) of the titled compound as a colorless solid, which was crystallized from methanol-ethyl acetate; m.p. 228° C. (decom.); $^1$H NMR (DMSO-$d_6$): δ 2.52 (m, 1H, H2'), 3.30–3.55 (m, 3H, H5', H4a"), 3.69 (dd, J=11.1 Hz, 2.7 Hz, 1H, H2a"), 3.73 (d, J=10.8 Hz, H4b"), 4.05 (d, J=10.8 Hz, 1H, H2b"), 4.40 (m, 1H, H2b"), 5.03 (t, J=6.0 Hz, 1H, OH), 5.74 (d, J=4.2 Hz, 1H, OH), 6.24 (s, 1H, H1'), 8.06 (s, 1H, H8), 8.30 (s, 1H, H2), 12.40 (s, 1H, NH); MS m/z 295 (MH$^+$).

Example 21

Preparation of (1S,3S,4R,8S)-8-hydroxy-1-hydroxymethyl-3-(hypoxanthin-9-yl)-2,6-dioxabicyclo[3,2,1]octane (21)

To a solution of (1R,3S,4R,8S)-1-acetoxymethyl-8-benzyloxy-3-(6-chloropurin-9-yl)-2,6-dioxabicyclo[3,2,1]octane (120 mg, 0.27 mmol), mercaptoethanol (0.15 mL, 2.1 mmol) in methanol (16 mL) was added sodium methoxide (1.62 mmol, 0.30 mL of 5.4 M in methanol). The similar procedure as described for Example 20 gave 37 mg (47%) of the titled compound as a hygroscopic solid; 1H NMR (DMSO-$d_6$) δ 2.52 (m, 1H, H2'), 3.06 (dd, J=11.7 Hz, 2.4 Hz, 1H, H2a"), 3.34–3.53 (m, 2H, H5'), 3.56 (d, J=11.1 Hz, 1H, H4a"), 3.79 (d, J=11.4 Hz, 1H, H4b"), 3.98 (d, J=11.4 Hz, 1H, H2b"), 4.31 (d, J=4.5 Hz, 1H, H3'), 4.89 (br, 1H, OH), 5.99 (br, 1H, OH), 6.28 (d, J=4.2 Hz, 1H, H1'), 8.03 (s, 1H, H8), 8.27 (s, 1H, H2), 12.30 (br, 1H, NH).

Example 22

Preparation of (1S,3S,4R,8S)-3-(guanin-9-yl)-8-hydroxy-1-hydroxymethyl-2,6-dioxabicyclo[3,2,1]octane (23)

A similar procedure as described for Example 18 gave the titled compound (41 mg, 66%) as an off-white solid from (1R,3S,4R,8S)-1-acetoxymethyl-3-(N²-acetylguanin-9-yl)-8-benzyloxy-2,6-dioxabicyclo[3,2,1]octane (100 mg). ¹H NMR (DMSO-d₆+D₂O) δ 2.42 (m, 1H, H2') 3.15 (dd, J=11.4 Hz, 2.1 Hz, 1H, H2a"), 3.34 (d, J=11.4 Hz, 1H, H5a'), 3.47 (d, J=12.6 Hz, 1H, H5b'), 3.51 (d, J=12.0 Hz, 1H, H4a"), 3.77 (d, J=10.8 Hz, 1H, H4b"), 3.98 (d, J=11.7 Hz, 1H, H2b"), 4.23 (d, J=4.8 Hz, 1H, H3'), 4.80 (br, 1H, OH), 5.90 (br, 1H, OH), 6.05 (d, J=4.2 Hz, 1H, H1'), 6.52 (br, 2H, NH₂), 7.93 (s, 1H, H8), 12.30 (br, 1H, NH); MS m/z 310 (MH⁺).

Example 23

Preparation of (1R,3R,4R,8S)-1-acetoxymethyl-8-benzyloxy-3-(thymin-1-yl)-2,6-dioxabicyclo[3,2,1]octane (24)

The reaction followed the same procedure as described for Example 14 except that the coupling reagent was tin (IV) chloride (0.45 mL) and the sugar substrate was (1R,3S,4R,8S)-1-acetoxymethyl-8-benzyloxy-3-methoxy-2,6-dioxabicyclo[3,2,1]octane (202 mg, 0.63 mmol). Chromatography on silica with 5% EtOH in CH₂Cl₂ gave a mixture (233 mg, 89%) of the titled compound (β-anomer) and its α-anomer (ratio of β:α, ~4:1) as a colorless solid. ¹H NMR (CDCl₃) of the β-anomer (from the spectrum of a mixture of the α- and β-anomers) δ 1.93 (d, J=0.9 Hz, 1H, ArCH₃), 2.05 (s, 3H, OAc), 2.66 (m, 1H, H2'), 3.48 (d, J=11.1 Hz, H4a"), 3.86–4.12 (m, 5H, H2a", H2b", H3', H4b", H5a'), 4.26 (d, J=12.6 Hz, H5b'), 4.44, 4.64 (AB, J=11.4 Hz, 2H, Bn), 6.06 (s, 1H, H1'), 7.26–7.42 (m, 5H, Bn), 7.59 (d, J=1.2 Hz, 1H, H6), 8.94 (s, 1H, NH).

Example 24

Preparation of (1R,3R,4R,8S)-1-acetoxymethyl-8-benzyloxy-3-(uracil-1-yl)-2,6-dioxabicyclo[3,2,1]octane (25)

A similar procedure as described for Example 23 gave, after chromatography on silica with 5% EtOH in methylene chloride, a mixture (267 mg, 87%) of the titled compound and its α-anomer (ratio of β:α, ~9:1) as a colorless solid from (1R,3S,4R,8S)-1-acetoxymethyl-8-benzyloxy-3-methoxy-2,6-dioxabicyclo[3,2,1]octane (230 mg, 0.71 mmol) and silylated uracil (2.0 mmol). The titled compound (β-anomer) was partially separated by chromatography on silica; m.p. 145–147° C. (EtOAc-hexanes); ¹H NMR (CDCl₃) δ 2.02 (s, 3H, OAc), 2.67 (m, 1H, H2'), 3.49 (d, J=11.4 Hz, 1H, H4a"), 3.86–3.97 (m, 3H, H2a", H3', H4b"), 4.08 (d, J=12.3 Hz, 1H, H5a'), 4.09 (d, J=10.5 Hz, 1H, H2b"), 4.25 (d, J=12.3 Hz, 1H, H5b'), 4.44, 4.64 (AB, J=11.7 Hz, 2H, Bn), 6.05 (s, 1H, H1'), 7.26–7.40 (m, 5H, Bn), 5.69 (d, J=8.1 Hz, 1H, H5), 7.79 (d, J=8.4 Hz, 1H, H6), 8.92 (s, 1H, NH); Anal. Calcd. for C₂₀H₂₂N₂O₇: C, 59.69; H, 5.51; N, 6.96. Found: C, 59.45; H, 5.56; N, 6.91.

Example 25

Preparation of (1R,3R,4R,8S)-1-acetoxymethyl-8-benzyloxy-3-(N⁴-benzoylcytosin-1-yl)-2,6-dioxabicyclo[3,2,1]octane (26)

A similar procedure as described for Example 23 gave, after chromatography on silica with 5% EtOH in methylene chloride, 910 mg (90%) of the titled compound (β-anomer) as a colorless solid from the reaction of (1R,3S,4R,8S)-1-acetoxymethyl-8-benzyloxy-3-methoxy-2,6-dioxabicyclo[3,2,1]octane (645 mg, 2.0 mmol) with silylated N⁴-benzoylcytosine (4.0 mmol); m.p. 173–174° C. (EtOAc); ¹H NMR (CDCl₃) δ 2.07 (s, 3H, OAc), 2.83 (m, 1H, H2'), 3.51 (d, J=11.1 Hz, H4a"), 3.86 (d, J=5.4 Hz, 1H, H3'), 3.97 (d, J=11.1 Hz, 1H, H4b"), 3.99–4.13 (m, 3H, H2a", H2b", H5a'), 4.27 (d, J=12.3 Hz, 1H, H5b'), 4.38, 4.61 (AB, J=11.4 Hz, 2H, Bn), 6.15 (s, 1H, H1'), 7.24–7.38 (m, 5H, Bn), 7.50–7.66 (m, 4H, H5, Bz), 7.90 (m, 2H, Bz), 8.28 (d, J=7.5 Hz, 1H, H6), 8.84 (br, 1H, NH); Anal. Calcd. for C₂₇H₂₇N₃O₇: C, 64.15; H, 5.38; N, 8.31. Found: C, 64.10; H, 5.20; N, 8.43.

Example 26

Preparation of (1S,3R,4R,8S)-8-hydroxy-1-hydroxymethyl-3-(thymin-1-yl)-2,6-dioxabicyclo[3,2,1]octane (27)

To a solution of the mixture of (1R,3R,4R,8S)-1-acetoxymethyl-8-benzyloxy-3-(thymin-1-yl)-2,6-dioxabicyclo[3,2,1]octane and its α-anomer (~4:1, 200 mg, 0.48 mmol) in anhydrous methylene chloride (4 mL) at 0° C. was added boron trichloride (1.0 M in CH₂CH₂, 8 mL). The resulting reaction mixture was stirred at room temperature for 8 h, at 15° C. overnight, and then cooled to 0° C. Methanol (5.0 mL) was added dropwise, followed by addition of 1.0 M NaOMe in MeOH until pH 8. The solution was separated and the precipitate extracted with 20% methanol in methylene chloride thoroughly. The combined filtrate was dried (Na₂SO₄), and concentrated to dryness. Chromatography on silica with 10–15% methanol in ethyl acetate gave the titled compound (78 mg), a mixture of the titled compound and its α-anomer (24 mg), and the a-anomer (23 mg), all as a colorless solid. Total yield was 91%. Crystallization of the titled compound from methanol-ethyl acetate gave the crystalline solid; m.p. 217–218° C.; ¹H NMR (DMSO-d₆): δ 1.75 (d, J=1.2 Hz, 1H, ArCH₃), 2.24 (m, 1H, H2'), 3.20 (d, J=10.8 Hz, 1H, H4a"), 3.33–3.58 (m, 3H, H2a", H5'), 3.66 (d, J=10.8 Hz, H4b"), 3.97 (d, J=10.5 Hz, 1H, H2b"), 4.14 (m, 1H, H3'), 5.24 (t, J=5.1 Hz, 1H, OH), 5.67 (d, J=2.4 Hz, 1H, OH), 5.82 (s, 1H, H1'), 7.95 (d, J=0.9 Hz, 1H, H6), 11.32 (s, 1H, NH); MS m/z 285 (MH⁺); Anal. Calcd. for C₁₂H₁₆N₂O₆: C, 50.70; H, 5.67; N, 9.85. Found: C, 50.65; H, 5.57; N, 9.73.

Example 27

Preparation of (1S 3R,4R,8S)-8-hydroxy-1-hydroxymethyl-3-(uracil-1-yl)-2,6-dioxabicyclo[3,2,1]octane (28)

A similar procedure as described for Example 26 gave, after chromatography on silica with 10% methanol in methylene chloride, 110 mg (76%) of the titled compound as a white solid from (1R,3R,4R,8S)-1-acetoxymethyl-8-benzyloxy-3-(uracil-1-yl)-2,6-dioxabicyclo[3,2,1]-octane (215 mg, 0.53 mmol). The titled compound was contaminated by a small amount of its α-anomer. The pure, titled compound was obtained by re-crystallization from acetone-ethyl acetate; m.p. 218–219° C.; ¹H NMR (acetone-d₆) δ 2.42 (m, 1H, H2'), 3.27 (d, J=10.8 Hz, 1H, H4a"), 3.58–3.72

(m, 3H, H2a", H5'), 3.83 (d, J=10.8 Hz, 1H, H4b"), 4.13 (d, J=10.5 Hz, 1H, HH2b"), 4.37 (t, J=5.1 Hz, 1H, OH), 4.42 (m, 1H, H3'), 4.88 (d, J=3.9 Hz, 1H, OH), 5.52 (d, J=7.8 Hz, 1H, H5), 5.95 (s, 1H, H1'), 8.17 (d, J=7.8 Hz, 1H, H6), 10.02 (s, 1H, NH); MS m/z 271 (MH$^+$); Anal. Calcd. for $C_{11}H_{14}N_2O_6$: C, 48.89; H, 5.22; N, 10.37. Found: C, 48.60; H, 5.64; N, 10.21.

Example 28

Preparation of (1S,3R,4R,8S)-3-(cytosin-1-yl)-8-hydroxy-1-hydroxymethyl-2,6-dioxabicyclo[3,2,1]octane (30)

A similar procedure as described for Example 26 gave, after chromatography on silica with 10% MeOH in methylene chloride from (1R,3R,4R,8S)-1-acetoxymethyl-8-benzyloxy-3-($N^4$-benzoylcytosin-1-yl)-2,6-dioxabicyclo-[3,2,1]octane, 364 mg (65%) of (1S,3R,4R,8S)-3-($N^4$-benzoylcytosin-1-yl)-8-hydroxy-1-hydroxymethyl-2,6-dioxabicyclo-[3,2,1]octane (760 mg), 120 mg (0.32 mmol) of which was dissolved in a saturated solution of ammonia in methanol and the solution stirred at room temperature for 24 h. Ammonia and methanol were evaporated and the residue was dissolved in water, followed by thorough extraction with chloroform (5 times) and then with toluene (2 times). Water was evaporated and crystallization from methanol gave 62 mg of the titled compound (45 mg of crystalline solid and 17 mg of non-crystalline solid); m.p. 250° C. (decom.); $^1$H NMR (CD$_3$OD) δ 2.33 (m, 1H, H2'), 3.31 (d, J=11.1 Hz, 1H, H4a"), 3.57 (d, J=12.3 Hz, 1H, H5a'), 3.65 (d, J=12.3 Hz, 1H, H5b'), 3.78 (dd, J=10.5 Hz, 2.7 Hz, H2a"), 3.84 (d, J=11.1 Hz, 1H, H4b"), 4.14 (d, J=10.5 Hz, 1H, H2b"), 4.20 (d, J=5.1 Hz, 1H, H3'), 5.86 (d, J=7.5 Hz, 1H, H5), 5.96 (s, 1H, H1'), 8.22 (d, J=7.8 Hz, 1H, H6); MS: m/z 270 (MH$_+$); Anal. Calcd. for $C_{11}H_{15}N_3O_5$: C, 49.07; H, 5.62; N, 15.61. Found: C, 48.93; H, 5.55; N, 15.64. Similarly, (1S,3R,4R,8S)-3-($N^4$-acetylcytosin-1-yl)-8-hydroxy-1-hydroxymethyl-2,6-dioxabicyclo-[3,2,1]octane was prepared.

Alternatively, a synthetic procedure may follow the protocol as outlined below: A mixture of (1S,3R,4R,8S)-8-hydroxy-1-hydroxymethyl-3-(uracil-1-yl)-2,6-dioxabicyclo[3,2,1]octane (170 mg, 0.63 mmol), acetic anhydride (2.16 mL, 20.1 mmol), and pyridine (0.29 mL, 3.5 mmol) in anhydrous DMF (2.5 mL) was stirred at room temperature overnight, diluted with methylene chloride, washed with brine and 10% NaHCO$_3$, dried (Na$_2$SO$_4$), concentrated to dryness. Chromatography on silica with ethyl acetate-hexanes (2:1) gave 117 mg (77%) of the 3',5'-diacetyl derivative of (1S,3R,4R,8S)-8-acetoxy-1-caetoxymethyl-3-(uracil-1-yl)-2,6-dioxabicyclo[3,2,1]-octane.

The (1S,3R,4R,8S)-8-acetoxy-1-caetoxymethyl-3-(uracil-1-yl)-2,6-dioxabicyclo-[3,2,1]-octane (175 mg, 0.58 mmol) was dissolved in anhydrous pyridine (1.5 mL) and the resulting solution cooled to 0° C. under argon, followed by addition of 4-chlorophenyl dichlorophosphate (0.29 mL, 1.75 mmol). The resulting solution was warmed up to room temperature and transferred to a septum-capped vial containing 1,2,4-triazole (120 mg, 1.75 mmol). The reaction mixture was stirred at room temperature for 3 days, diluted with CH$_2$Cl$_2$, washed with brine and 5% NaHCO$_3$, dried (Na$_2$SO$_4$), and concentrated to dryness. The residue was dissolved in dioxane (7 mL) and 30% ammonium hydroxide (10 mL). The solution stood at room temperature for 16 h and the solvents were evaporated. The residue was chromatographed on silica with Et$_3$N—MeOH—CHCl$_3$ (5:30:65) to give 74 mg (55%) of the titled compound as a slightly yellow solid.

Example 29

Preparation of (1R,3R,4R,8S)-1-acetoxymethyl-3-($N^2$-acetylguanin-7-yl)-8-benzyloxy-2,6-dioxabicyclo[3,2,1]-octane (31)

The silylated base from $N^2$-acetylguanine (386 mg, 2.0 mmol) was prepared according to the procedure described for Example 17 and dissolved in a solution of (1R,3S,4R,8S)-1-acetoxymethyl-8-benzyloxy-3-methoxy-2,6-dioxabicyclo[3,2,1]octane (477 mg, 1.48 mmol) in anhydrous 1,2-dichloroethane (10 mL), followed by addition of tin (IV) chloride (0.75 mL) in 1,2-dichloroethane (2.0 mL). The resulting mixture was heated at reflux for 3 h, then at 70° C. overnight, and cooled to 0° C. The mixture was neutralized with 2.0 M sodium carbonate, filtered through celite, and thoroughly extracted with chloroform. The combined filtrate was dried (Na$_2$SO$_4$) and concentrated to dryness. Chromatography on silica with 5% EtOH in chloroform gave 297 mg (42%) of the titled compound, 73 mg (10%) of the N9-coupled β-anomer of the titled compound, and 46 mg (6%) of the N9-coupled α-anomer, all as a white solid. The titled compound: m.p. 176–178° C. (CH$_3$Cl-EtOAc); $^1$H NMR (CDCl$_3$) δ 2.09 (s, 3H, OAc), 2.40 (s, 3H, NAc), 2.78 (m, 1H, H2'), 3.53 (d, J=11.4 Hz, 1H, H4a"), 3.99 (d, J=11.1 Hz, H4b"), 4.03–4.18 (m, 4H, H2a", H2b", H3', H5a'), 4.26 (d, J=12.6 Hz, 1H, H5b'), 4.39, 4.58 (AB, J=11.7 Hz, 2H, Bn), 6.62 (s, 1H, H1'), 7.22–7.40 (m, 5H, Bn), 8.21 (s, 1H, H8), 10.60 (s, 1H, NH), 12.34 (s, 1H, NH); Anal. Calcd. for $C_{23}H_{251}N_5O_8$: C, 55.31; H, 5.05; N, 14.02. Found: C, 55.35; H, 4.83; N, 13.80.

Example 30

Preparation of (1R,3R,4R,8S)-1-acetoxymethyl-3-($N^2$-acetylguanin-9-yl)-8-benzyloxy-2,6-dioxabicyclo[3,2,1]-octane (32)

The same amount of the silylated $N^2$-acetylguanine as described for Example 29 was dissolved in a solution of (1R,3R,4R,8S)-1-acetoxymethyl-3-($N^2$-acetylguanin-7-yl)-8-benzyloxy-2,6-dioxabicyclo[3,2,1]-octane (370 mg, 0.76 mmol) in anhydrous 1,2-dicloroethane (10 mL) and trimethylsilyl triflate (0.54 mL, 3.0 mmol) in 1,2-dichloroethane (3 mL) was added. The resulting solution was heated under reflux overnight. Additional TMSOTf (0.54 mL) was added and the mixture refluxed for additional two days. The same work-up as described for Example 29 gave, after chromatography on silica with 5% ethanol in chloroform, 104 mg (28%) of the intact starting material, 91 mg (25%) of the titled compound, and 80 mg (22%) of the α-anomer of the titled compound, all as a white solid. The titled compound: m.p. 128–131° C. (CH$_3$Cl-EtOAc); $^1$H NMR (CDCl$_3$) δ 2.02 (s, 3H, OAc), 2.30 (s, 3H, NAc), 2.67 (m, 1H, H2'), 3.50 (d, J=10.8 Hz, 1H, H4a"), 3.78 (dd, J=10.8 Hz, 2.7 Hz, 1H, H2a"), 3.99 (d, J=10.8 Hz, H4b"), 4.12 (d, J=12.3 Hz, 1H, H5a'), 4.14 (d, J=10.8 Hz, 1H, H2b"), 4.27 (d, J=12.3 Hz, 1H, H5b'), 4.33 (d, J=5.1 Hz, 1H, H3'), 4.49, 4.62 (AB, J=11.7 Hz, 2H, Bn), 6.25 (s, 1H, H1'), 7.26–7.38 (m, 5H, Bn), 7.83 (s, 1H, H8), 9.0 (s, 1H, NH), 11.95 (s, 1H, NH); MS: m/z 310 (MH$^+$); Anal. Calcd. for $C_{23}H_{25}N_5O_8$: C, 55.31; H, 5.05; N, 14.02. Found: C, 55.70; H, 5.00; N, 13.95.

Example 31

Preparation of (1S,3R,4R,8S)-3-(guanin-9-yl)-8-hydroxy-1-hydroxymethyl-2,6-dioxabicyclo[3,2,1]octane (33)

A similar procedure as described for Example 22 gave, after chromatography, 52 mg (45%) of the titled compound as a colorless solid from (1R,3R,4R,8S)-1-acetoxymethyl-3-(N$^2$-acetylguanin-9-yl)-8-benzyloxy-2,6-dioxabicyclo[3,2,1]-octane (180 mg). Crystallization from water-ethanol (9:1) gave a crystalline solid; m.p. 258° C. (decom.); $^1$H NMR (DMSO): δ 2.45 (m, 1H, H2'), 3.31 (d, J=10.8 Hz, 1H, H4a"), 3.36–3.50 (m, 2H, H5a', H5b'), 3.60 (dd, J=10.2 Hz, 2.7 Hz, 1H, H2a"), 3.1 (d, J=11.1 Hz, H4b"), 4.03 (d, J=10.5 Hz, 1H, H2b"), 4.36 (m, 1H, H3H'), 4.95 (t, J=5.7 Hz, 1H, OH), 5.70 (d, J=3.9 Hz, 1H, OH), 6.06 (s, 1H, H1'), 6.55 (br, 2H, NH$_2$), 7.90 (s, 1H, H8), 10.68 (s, 1H, NH); MS m/z 310 (MH$^+$).

Example 32

Preparation of (1S,3R,4R,8S)-8-hydroxy-1-(4,4'-dimethoxytrityloxymethyl)-3-(N$^4$-acetylcytosin-yl)-2,6-dioxbicyclo[3,2,1]octane (35)

A solution of (1S,3R,4R,8S)-8-hydroxy-1-hydroxymethyl-3-(N$^4$-acetylcytosin-yl)-2,6-dioxabicyclo[3,2,1]octane (200 mg, 0.64 mmol) and 4,4'-dimethoxytrityl chloride (548 mg, 0.61 mmol) in anhydrous pyridine (7 mL) stood at room temperature overnight, diluted with ethyl acetate, washed with brine and 10% NaHCO$_3$, dried over sodium sulfate, and concentrated. Chromatography on silica with 10% ethanol in chloroform gave 342 mg (87%) of the titled compound as colorless foam.

Similarly, (1S,3R,4R,8S)-8-hydroxy-1-(4,4'-dimethoxytrityloxymethyl)-3-(N$^4$-benzoyl-cytosin-1-yl)-2,6-dioxabicyclo[3,2,1]octane (36) and (1S,3R,4R,8S)-8-hydroxy-1-(4,4'-dimethoxytrityloxymethyl)-3-(thymin-yl)-2,6-dioxabicyclo[3,2,1]octane (34) were prepared.

Example 33

Preparation of (1S,3R,4R,8S)-8-hydroxy-1-(4,4'-dimethoxytrityloxymethyl)-3-(N$^4$-acetylcytosin-yl)-2,6-dioxabicyclo[3,2,1]octane 8-O-(2-cyanoethyl-N,N-diisopropylphophoramidite)(38)

To a stirred solution of (1S,3R,4R,8S)-8-hydroxy-1-(4,4'-dimethoxytrityloxy-methyl)-3-(N$^4$-acetyl-cytosin-yl)-2,6-dioxabicyclo[3,2,1]octane (320 mg, 0.52 mmol) and diisopropylethyl-amine (0.36 mL, 2.08 mmol) in anhydrous dichloromethane (6 mL) at 0° C. under argon was added dropwise 2-cyanoethyl-N,N-diisopropylchlorophosphoramidite (0.23 mL, 1.04 mmol). The resulting solution was stirred at ambient temperature for 4 h, cooled with ice, diluted with ethyl acetate, washed with cold 10% NaHCO$_3$, dried over sodium sulfate, and concentrated at room temperature. Chromatography on silica with 5% triethylamine and 5% acetone in methylene chloride gave 376 mg (89%) of the titled compound as a colorless foam.

Similarly, (1S,3R,4R,8S)-8-hydroxy-1-(4,4'-dimethoxytrityloxymethyl)-3-(N$^4$-benzoyl-cytosin-1-yl)-2,6-dioxabicyclo[3,2,1]octane 8-O-(2-cyanoethyl-N,N-diisopropyl-phophoramidite) (39) and (1S,3R,4R,8S)-8-hydroxy-1-(4,4'-dimethoxytrityloxymethyl)-3-(thymin-1-yl)-2,6-dioxabicyclo[3,2,1]octane 8-O-(2-cyanoethyl-N,N-diisopropyl-phophoramidite) (37) were prepared.

Thus, specific embodiments and applications of displays and methods for producing novel nucleosides with bicyclic sugar moieties have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

What is claimed is:

1. A compound having the following formula:

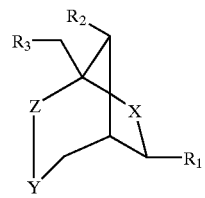

wherein X is O:
Y is O and Z is CH$_2$;
R$_1$ is a heterocyclic base; and
R$_2$ and R$_3$ are independently H, OH, halogen, protected hydroxyl, CN, N$_3$, OCH$_3$, or W, wherein W is monosphophate, diphosphate, triphosphate, monophosphate, diphosphonate, triphosphonate, an amino acid ester with an OH group the sugar portion, or a prodrug of the monophosphate, diphosphate, triphosphate, monophosphonate, diphosphonate, or triphosphonate.

2. The compound according to claim 1, wherein the heterocyclic base comprises a purine, a pyrimidine, a deazapurine, an azapurines, a deazapyrimidine, an azapyrimidine, or a triazole.

3. A method of treating a viral infection in a patient, comprising: providing a compound according to claim 1; and administering the compound to the patient at a dosage effective to reduce viral administering the compound to the patient at a dosage effective to reduce viral propagation.

4. The method of claim 3 wherein the virus is a hepatic C virus.

5. The method of claim 3 further comprising co-administration of an interferon.

6. The method of claim 5 wherein the interferon is interferon alpha or interferon gamma.

7. A pharmaceutical composition comprising a compound according to claim 1 and a pharmaceutically acceptable carrier.

8. The composition of claim 7 wherein the compound forms a pharmaceutically acceptable salt with an acid or a base, or wherein the compound is in the form of a prodrug.

9. The composition of claim 8 wherein the prodrug comprises an ester with at least one of $R_2$ and $R_3$.

10. The composition of claim 9 wherein the ester comprises a phosphate or phosphate ester.

11. The composition of claim 8 wherein the prodrug enhances specificity or the compound to the liver.

* * * * *